(12) United States Patent
St. Cyr et al.

(10) Patent No.: US 7,687,468 B2
(45) Date of Patent: Mar. 30, 2010

(54) REJUVENATION OF STORED BLOOD

(75) Inventors: John A. St. Cyr, Coon Rapids, MN (US); Daniel G. Ericson, Rochester, MN (US); Clarence A. Johnson, Wyoming, MN (US)

(73) Assignee: Viacell, LLC., Ham Lake, MN (US)

( * ) Notice: Subject to any disclaimer, the term of this patent is extended or adjusted under 35 U.S.C. 154(b) by 110 days.

(21) Appl. No.: 10/437,621

(22) Filed: May 14, 2003

(65) Prior Publication Data

US 2004/0229204 A1 Nov. 18, 2004

(51) Int. Cl.
- *A01N 1/02* (2006.01)
- *A61K 31/7004* (2006.01)
- *A61K 31/122* (2006.01)
- *A61K 31/047* (2006.01)
- *A61K 35/18* (2006.01)

(52) U.S. Cl. .................. 514/23; 514/675; 514/738; 424/533; 435/2

(58) Field of Classification Search .............. 435/2; 604/6.02; 424/529; 514/461, 693
See application file for complete search history.

(56) References Cited

U.S. PATENT DOCUMENTS

| | | | |
|---|---|---|---|
| 4,386,069 A | 5/1983 | Estep | |
| 4,769,318 A | 9/1988 | Hamasaki et al. | |
| 4,853,370 A * | 8/1989 | Ecanow et al. | 514/6 |
| 4,870,002 A * | 9/1989 | Kiel | 435/2 |
| 6,159,942 A | 12/2000 | St. Cyr | |
| 2005/0208462 A1 | 9/2005 | Bitensky et al. | |
| 2007/0111191 A1 | 5/2007 | St. Cyr et al. | |
| 2007/0178434 A1 | 8/2007 | Natan et al. | |

OTHER PUBLICATIONS

Medline abstract 75128511 (1975).*
Dawson, R.B. et al. "Blood Preservation 33. Phisphate Enhancement of Ribose Maintenance of 2,3-DPG and ATP" Transfusion, 21 (2), pp. 215-218 (Mar.-Apr. 1981).
Dawson, R.B. et al. "Blood Preservation 50: Red Cell 2,3-DPG Maintenance in CPD-Adenine Stored Blood by Several Mechanisms"The Red Cell: 5th AnnualArborConf, pp. 643-660,1981.
Elfath, "Is it time to focus on preserving the functionality of red blood cells during storage?" *Transfusion*, 2006; 46:1469-1470.
Hawkes et al., "Heart surgery patients put in danger by using 14-day-old blood," *TimesOnline* (London), Mar. 24, 2008 [retrieved on Oct. 13, 2008].Retrieved from the Internet:<URL:http://www.timesonline.co.uk/tol/life_and_style/health/article3607486>; 2 pgs.
Koch et al., "Duration of red-cell storage and complications after cardiac surgery," *N. Engl. J. Med.*, Mar. 20, 2008; 358:1229-1239.
Petrich et al., "Der Einfluss von Ribose auf die 2,3-Diphosphoglycerat-Konzentration menschlicher Erythrozyten," *Blut*, 1995; 30:175-182). (English translation included (12 pgs).
Valeri et al., "The survival, function, and hemolysis of human RBCs stored at 4 degrees C in additive solution (AS-1, AS-3, or AS-5) for 42 days and then biochemically modified, frozen, thawed, washed, and stored at 4 degrees C in sodium chloride and glucose solution for 24 hours," *Transfusion*, Nov. 2000; 40(11):1341-5. Abstract only (1 page).
Department of Health and Human Services, Food and Drug Administration, "Rejuvesol®, Red Blood Cell Processing Solution," enCyte™ Systems, Inc.; 32 pages. Oct. 5, 1998.

* cited by examiner

*Primary Examiner*—John Pak
(74) *Attorney, Agent, or Firm*—Mueting, Raasch & Gebhardt, P.A.

(57) ABSTRACT

D-Ribose, a buffer and an anticoagulant are added to whole blood or packed red cells to extend function in storage beyond 42 days. Methods are disclosed to rejuvenate suboptimally functional red cells. The methods are comprised of incubation of the cells at 37° C. for 10 to 60 minutes in the presence of D-ribose.

9 Claims, 4 Drawing Sheets

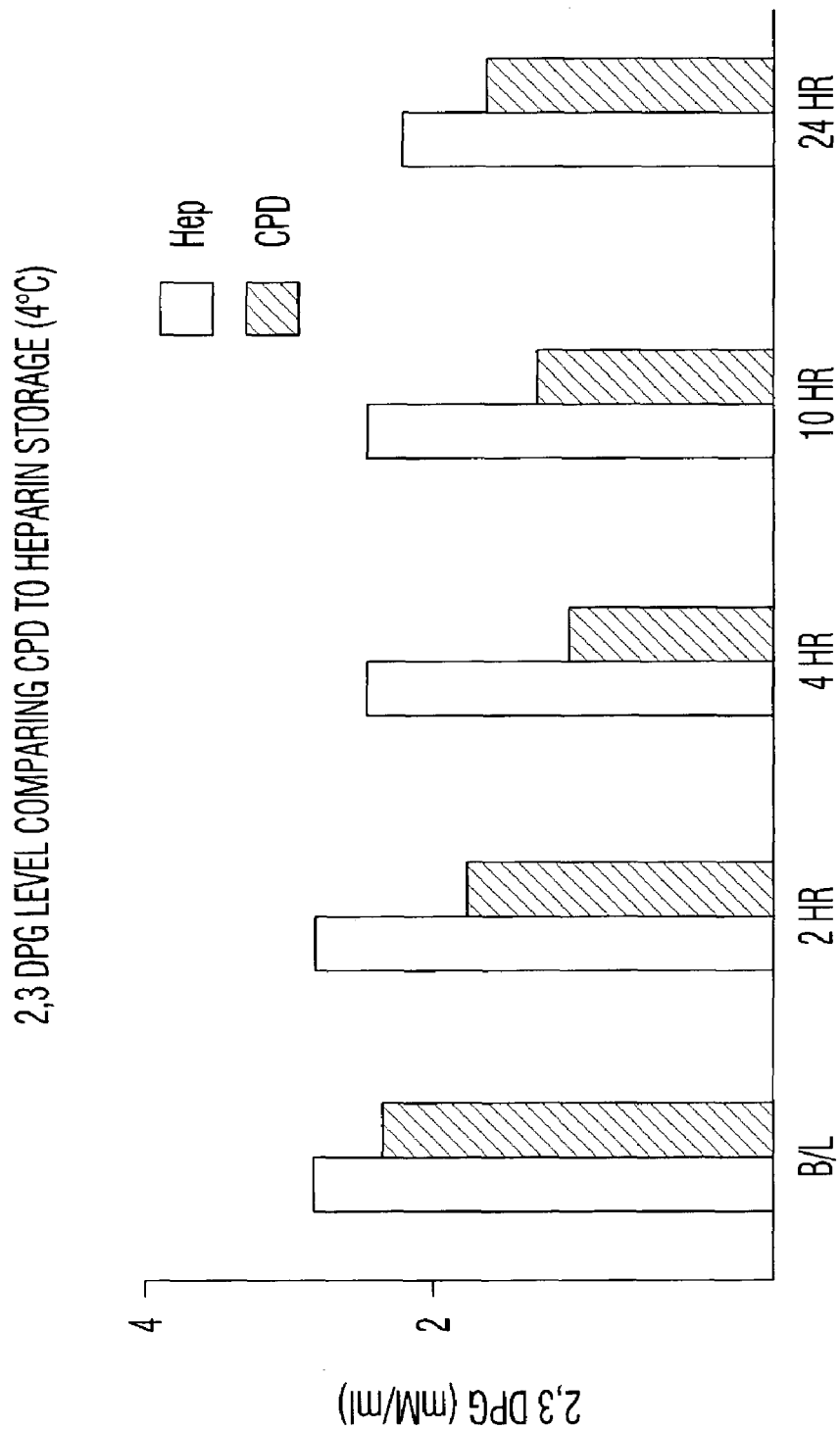

REJUVENATION OF STORED BLOOD

FIELD OF THE INVENTION

This invention pertains to the storage, preservation and rejuvenation of whole blood and packed red blood cells.

BACKGROUND OF THE INVENTION

About 12.6 million units (including approximately 643,000 autologous donations) of whole blood are donated in the United States each year by approximately eight million volunteer blood donors. These units are transfused to about four million patients per year. Typically, each donated unit of blood, referred to as whole blood, may be separated into multiple components, such as red blood cells, plasma, clotting factors, gamma globulin and platelets. The need for blood is great: on any given day, approximately 32,000 units of red blood cells are needed. Accident victims, people undergoing surgery and patients receiving treatment for leukemia, cancer or other diseases such as sickle cell disease and thalassemia, all utilize blood.

Because patients seldom require all of the components of whole blood, it is the usual practice in blood banks to separate the blood into components and transfuse only that portion needed by the patient for a specific condition or disease. This treatment, referred to as "blood component therapy" allows several patients to benefit from each unit of blood.

Whole blood is a living tissue that circulates through the heart, arteries, veins and capillaries, carrying nourishment, electrolytes, antibodies, heat and oxygen to the body tissues. Whole blood is comprised of red blood cells, white blood cells and platelets suspended in a proteinaceous fluid termed blood plasma. If blood is treated to prevent clotting and permitted to stand in a container, red blood cells will settle to the bottom of the container, the plasma will remain on top and the white blood cells will form a layer on top of the red blood cells. A centrifuge is commonly used to hasten this separation. The platelet-rich plasma is then removed and placed into a sterile bag for further processing to separate, for example, platelets, clotting factors, albumin, immunoglobulins and the like.

The most important component for the usual transfusion need are the erythrocytes or red blood cells (RBC), which contain hemoglobin, a complex iron-containing protein that carries oxygen throughout the body and gives blood its red color. The percentage of blood volume that is composed of red blood cells is called the "hematocrit." The average hematocrit in the adult male is 47%. There are about one billion red blood cells in two or three drops of blood, and, for every 600 red blood cells, there are about 40 platelets and one white blood cell.

Manufactured in the bone marrow, RBCs are enucleated, biconcave discs that are continuously being produced, broken down and destroyed. The biconcave disc shape is crucial to the function of RBCs, presenting a maximal surface area for the capture of oxygen in the lungs and its release in the tissue. The cells are flexible and able to bend in order to traverse the tiny tubules of the capillary beds. Since the cells are enucleated and lack mitochondria, they are unable to carry out cellular repair of damage or enzyme inactivation and must rely on anaerobic phosphorylation for energy. After an average 120 days in the circulatory system, the cells are senescent and are phagocytized by circulating monocytes or the fixed macrophages of the reticulo-endothelial system.

Red blood cells are prepared from whole blood by removing the plasma. When transfused into a patient, the hematocrit is raised while increase in blood volume is minimized, which is especially important to such patients as those with congestive heart failure. The cells are typically suspended in about half the original volume; the preparation is referred to as packed red cells. Patients benefitting most from transfusions of packed red cells include those with chronic anemia from disorders such as kidney failure, malignancies, gastrointestinal bleeding or acute blood loss as from trauma or surgery.

Standard solutions for the storage of whole blood comprise citrate-phosphate-dextrose solution (CPD) and citrate-phosphate-dextrose-adenine solution(CPDA). Citrate or other anticoagulants such as heparin are necessary to prevent clotting. Because blood is a living tissue that maintains metabolic functions even at refrigerated temperatures, it has been considered necessary to provide an energy source such as glucose. Phosphate ion can be used to buffer the lactate produced from glucose utilization.

Improvements in cell preservation solutions over the last 15 years have increased the refrigerated shelf life of whole blood or red blood cells from 21 to 42 days. After 42 days, the blood is discarded, since many of the cells have become senescent and would be immediately phagocytized upon transfusion into a recipient. Although the red cells may appear to survive in storage for five or six weeks, they rapidly develop "storage lesion" characterized by biochemical and biomechanical changes that compromise their ability to accept, transport and unload oxygen to the tissue. For that reason, it is desirable to use the whole blood and blood products within three weeks or less of drawing.

The need remains for a solution in which blood cells in whole blood or packed red cell suspensions can be stored for an increased time and survive functionally when transfused into a recipient. The need also remains for a method to rejuvenate blood and RBCs which are suboptimally functional.

SUMMARY OF THE INVENTION

Figure 1B:
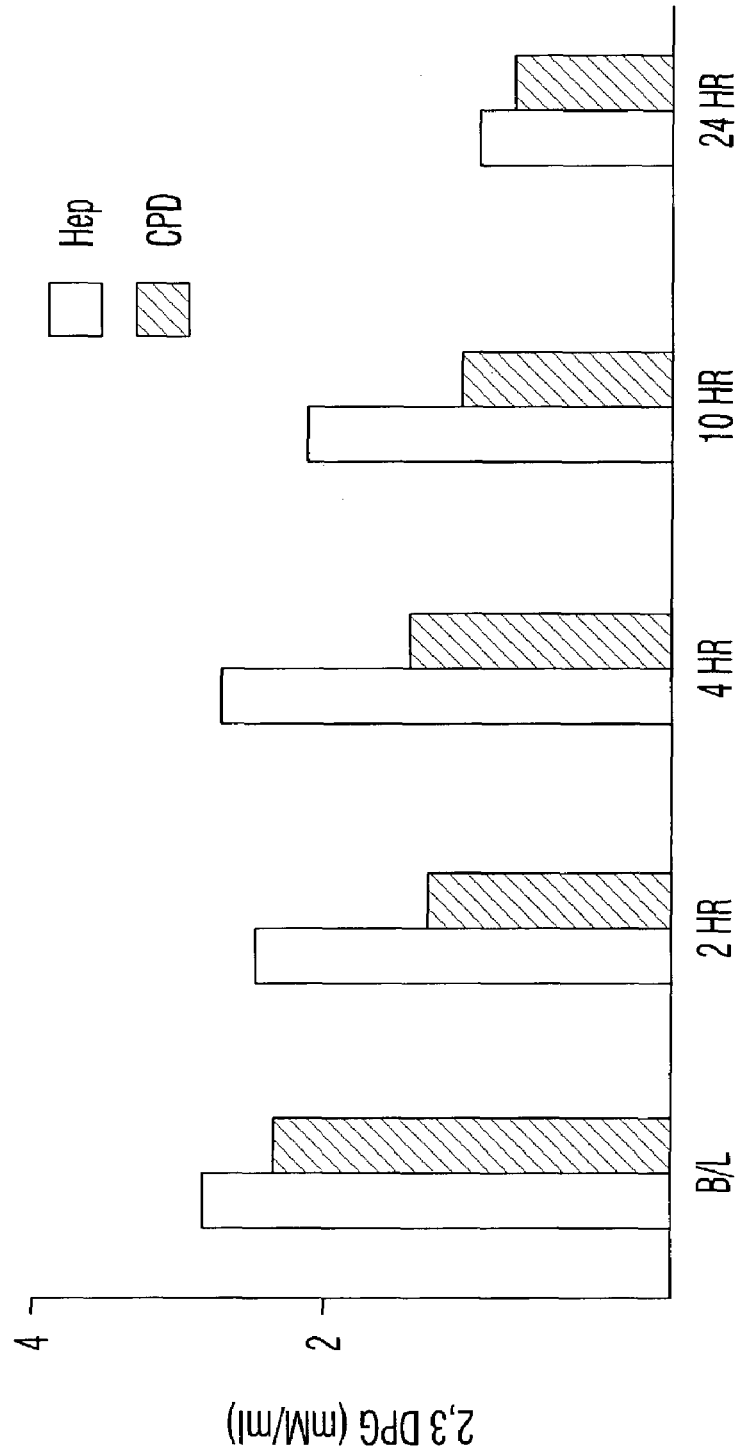
FIG. 1 shows the decrease in 2,3 diphosphoglycerate in whole blood stored at room temperature.

The present invention provides a composition in which whole blood and red blood cells can be stored for 42 to 120 days while remaining functional. The solution comprises an anticoagulant, and a compound that is useable by blood cells to maintain structural and functional integrity. The preferred anticoagulant is citrate at a concentration of from 2% to 6%. The preferred compound is poorly utilized by contaminating bacteria. The compound can be D-ribose, a ribose equivalent or a ribose-sparing monosaccharide, collectively referred to as "ribose-related compound." Ribose equivalents include ribose-5-phosphate, ribulose-5-phosphate, ribulose, xylulose-5-phosphate, xylulose, xylose and the related alcohol xylitol. The preferred ribose-related compound is D-ribose. The preferred ribose equivalent is xylose. Ribose-related compounds are most preferably used at a concentration of from 3 mM to 20 mM. The most preferred solution comprises 4% sodium citrate and 15 mM D-ribose. The preferred solution, when hydrated, has a pH between 7.0 and 7.8. The compositions of this invention do not contain dextrose.

An additional composition of this invention comprises an anticoagulant, a buffer and a compound that is useable by blood cells to maintain structural and functional integrity. The preferred anticoagulant is sodium citrate at a concentration of from 2% to 6%. The preferred buffer is sodium phosphate ($NaH_2PO_4/Na_2HPO_4$, to maintain a pH between 6.8 and 7.6) at a concentration of from 5 to 20 mM. The preferred compound is poorly utilized by contaminating bacteria. The preferred compound is a ribose-related compound and can be D-ribose, a ribose equivalent or a ribose-sparing monosaccharide. Ribose equivalents include ribose-5-phosphate, ribulose-5-phosphate, ribulose, xylulose-5-phosphate, xylulose, xylose and the related alcohol xylitol. The preferred ribose equivalent is xylose. The ribose-related compound is most preferably at a concentration of from 5 mM to 20 mM. The most preferred solution comprises 4% sodium citrate, 10 mM sodium phosphate and 15 mM D-ribose. The preferred solution, when hydrated, will have a pH between 7.0 and 7.8. The compositions of this invention do not contain added dextrose.

The compositions of this invention are added to whole blood as it is collected. The compositions are most conveniently placed in dry form or concentrated aqueous solution within the blood collection receptacle in amounts sufficient to provide the above concentrations. RBCs that are packed are typically suspended in plasma or saline at about half the volume of the whole blood from which they were separated. The compositions of this invention are added to the plasma or saline in amounts sufficient to provide the above compositions.

Stored blood that is suboptimally functional may be rejuvenated by treatment with the compositions of this invention. By rejuvenation is meant the treatment of the blood to raise the levels of 2,3 diphosphoglycerate (DPG). Suboptimal blood includes blood that has been left at room temperature for more than an hour or stored at 4° C. for more than a week and blood that has been damaged by blood fractionation or leukofiltration procedures or pathogen inactivation treatment. Just prior to transfusion or continued storage, the blood is warmed to 20° C. to 37° C., sufficient ribose-related compound to provide a concentration of from 5 to 20 mM is added and the blood bag gently shaken for 10 to 60 minutes, the rejuvenation period. The ribose-related compound is most conveniently added as a concentrated solution through the side arm of the blood bag. The most preferred ribose-related compound is 15 mM D-ribose, and the most preferred rejuvenation period is 30 minutes.

In another embodiment of the invention, just prior to transfusion or continued storage, the blood is warmed to 37° C., sufficient ribose-related compound to provide a concentration of from 5 to 20 mM and sufficient sodium phosphate to provide a concentration of from 5 to 10 mM is added and the blood bag gently shaken for 10 to 60 minutes In another embodiment of the invention, a method for rejuvenating red blood cells is provided, the method comprising:
  providing red blood cells that have been stored in the absence of a ribose-related compound for at least 21 days or at least 42 days to result in a decrease in the 2,3-diphosphoglycerate (DPG) level from the freshly drawn value;
  adding sufficient ribose-related compound to a suspension of red blood cells so as to reach a concentration of 5 to 20 mM, wherein the ribose-related compound is selected from the group consisting of D-ribose, ribose-5-phosphate, ribulose-5-phosphate, ribulose, xylulose-5-phosphate, xylulose, xylose, and xylitol; and
  incubating the cells at 37° C. for 10 to 60 minutes wherein the DPG levels are increased to at least one third of the freshly drawn value.

DETAILED DESCRIPTION OF THE INVENTION

Since the average life span of an RBC in vivo is 120 days, it should be theoretically possible to reach or exceed that life span in stored blood. It is thought that senescence in vivo is due to wear and tear on the cells in circulation, especially the deformation that occurs as the RBC passes through the capillary bed. Also, the enzymes of the glycolytic pathway which provide the energy necessary to support cell function can slowly degrade and are not replaceable by the enucleated cell. Hemoglobin can also degrade to methemoglobin. The situation in storage is not the same in every detail. Since the cells do not circulate and are at refrigerated temperatures, it is possible that the life span can be lengthened. However, during storage the solution becomes acidic and anoxic and the substrates of glycolysis may be exhausted. Toxic substances formed during anoxia accumulate and are not carried away by the circulation as in vivo. Intracellular glutathione, which maintains the appropriate cellular redox level, decreases, leading to the accumulation of free radicals. Lowered pH, the accumulation of free radicals and exhaustion of energy substrates are probably the main causes of storage lesion in stored RBC.

Mammalian RBCs contain high levels of the glycolytic intermediate 2,3 diphosphoglycerate (DPG) in concentrations roughly equimolar with hemoglobin. DPG binds the beta chain of de-oxyhemoglobin in a pH dependent manner. Binding decreases with increasing pH. As oxygen levels fall in vivo, hyperventilation occurs that reduces carbon dioxide and increases pH, thereby causing higher oxygen affinity and lower tissue delivery of oxygen. This reaction is accentuated by lower DPG levels; conversely, higher DPG levels maintain or lower the oxygen affinity for hemoglobin, thereby increasing tissue delivery. By RBC function is meant the ability of the RBC to bind oxygen at high oxygen tension (i.e., in the lungs in vivo) and release it at low oxygen tension (i.e., in the tissues in vivo). Therefore, DPG is both an enhancer of the lung-blood-tissue oxygen and tissue-blood-lungs carbon dioxide cycles and, because it correlates with function, a useful diagnostic parameter of RBC function.

Another useful parameter of RBC function is the oxygen dissociation curve (ODC), a measure of the ability of oxyhemoglobin to dissociate under low oxygen tension. Other parameters include ATP and glutathione levels, pH and hemoglobin oxygen affinity. The FDA adds the additional criteria of greater than 75% RBC survival recovery with less than 1% hemolysis. Survival is determined experimentally by labeling the RBCs with radioactive chromium and determining the radioactivity circulating at 24 hours after transfusion. Lowered survival not only fails to deliver the increased oxygen capacity sought by transfusion, but also releases deleterious substances such as free hemoglobin.

In order to address the problem, applicants have developed a solution that will maintain function and survivability of RBCs beyond 42 days of storage. The exemplar composition contains D-ribose. It has surprisingly been found by the inventors of this invention that the pentose monosaccharide D-ribose can be substituted for dextrose, the energy source for blood stored in CPD or CDPA. By ribose is meant D-ribose or ribose equivalents which include but are not limited to ribose-5-phosphate, ribulose-5-phosphate, ribulose, xylulose-5-phosphate, xylulose, xylose and the related alcohol xylitol, all of which are collectively referred to as ribose-related compounds. Ribose may be slowly converted in the cells to glucose, which enters the glycolytic pathway or may participate in other energy cycles. Thus one of the roles of ribose may be as an energy source for glycolysis. It is theorized that the main activity of ribose is in the regeneration of ATP, as is more fully explained in, e.g., U.S. Pat. No. 6,159,942. As will be shown in the following examples, ribose replacing dextrose results in better retention of functionality of RBC than dextrose, the usual energy source for blood storage. Ribose has a further advantage over dextrose in that dextrose is a preferred substrate for contaminating bacteria, while ribose is a poor substrate for most bacteria.

When RBC or whole blood is stored, DPG levels tend to decrease, as outlined above, and when blood or RBCs with low DPG is transfused into a patient, it is suboptimally functional unless or until the DPG levels are restored, which may take as long as 24 hours. Inventors have found that such RBCs can be rejuvenated.

EXAMPLE 1

Composition for Storage of Whole Blood and Packed RBC.

At the present time, blood is collected in bags containing CPD or CPDA. The citrate serves as anticoagulant, while the phosphate buffers the lactate that is formed from energy production via glycolysis. Dextrose is added as a substrate for glycolysis. Surprisingly, the inventors have discovered that dextrose can be eliminated when D-ribose is present and the cells remain optimally functional for a longer time. If dextrose is present, the ribose effect is neither diminished nor enhanced.

Whole blood is collected into a bag containing dry powders or concentrated aqueous solution sufficient to provide a final concentration of 4% sodium citrate, 10 mM sodium phosphate at a pH of 7.4, and 15 mM D-ribose (CPR). When packed RBC are prepared, they are resuspended in plasma containing CPR or a balanced salt solution containing CPR. The bags are stored at refrigerated temperatures, preferably 4° C.

EXAMPLE 2

Determination of Viability of RBC.

It has been previously shown (Dawson, Blood (1981)) that RBC stored in standard citrate-phosphate-dextrose (CPD) maintains about 26% of its initial 2,3 DPG level at 42 days of storage at 4° C. Adding 15 mM D-ribose and 10 mM phosphate increased the DPG levels at 42 days to about 50%. The inventors have repeated Dawson's studies with the following results:

TABLE I

| | 2,3 DPG levels, μmol/ml | |
|---|---|---|
| Day, stored at 4° C. | CPDA (CPD plus adenine) | CPDA plus D-Ribose |
| 8 | 94 | 94 |
| 15 | 64 | 95 |
| 22 | 57 | 77 |
| 29 | 33 | 66 |
| 37 | 8 | 39 |
| 44 | 4 | 33 |
| 51 | — | 16 |
| 56 | — | 5 |

The results seen in the above verification of Dawson can be accelerated by storing the blood samples at room temperature. To test that assumption, blood collected in the CPD, CPDA, or with phosphate/dextrose plus heparin as an anticoagulant was assayed for DPG content at 4° C. and at room temperature. DPG was measured by following the enzymatic cleavage of 2,3 DPG by activated phosphoglycerate mutase (PGM) in the presence of glycolate-2-phosphate.

The DPG assay was as follows:

To 2 mL Tris buffer with EDTA, was added 0.05 ml ATP 40 mM plus NADH 9.6 mM; 0.04 ml PGM (Sigma kit 665PA, Sigma, Inc. St. Louis, Mo.) and 0.1 ml RBC. The reaction mixture was allowed to equilibrate for five minutes at room temperature and the absorption at 339 nm wavelength was recorded. Next was added 0.02 ml PGM and 0.02 ml glycolate-2-phosphate. The reaction was allowed to proceed for 25 minutes and the absorption at 339 nm wavelength was recorded. The packed cell DPG equals (μmol/ml)×100 divided by the hematocrit.

FIG. 1a shows that levels of DPG stored at 4° C. levels of DPG remained high over 24 hours of storage, with the heparin stored RBC maintaining the initial levels somewhat better than those stored in CPDA. At room temperature, loss of DPG was accelerated, as shown in Figure 1b. Those cells stored in CPDA lost 75% of the initial levels of DPG, while those stored in heparin were slightly better, losing only about 67% of the initial levels.

3

Effect of D-Ribose on Storage of RBC.

A unit of collected blood containing the composition of Example 1 will be stored at 4° C. At the time points 0 days, 15 days, 30 days, 45 days, 60 days, 90 days and 120 days, viability will be determined. The following tests will be performed: Trypan blue exclusion to determine % live versus dead RBC; free hemoglobin to determine lysed RBC; hematocrit to determine diminution of size and number of RBCs; pH; and 2,3-DPG.

EXAMPLE 4

Rejuvenation of Stored RBC.

A. Example 2 showed that storage at room temperature accelerated the decrease in DPG, the measure of RBC function. Whole blood stored at 4° C. may also have decreased DPG levels. Additionally, many blood banks have a practice of holding blood or RBC at room temperature for eight to 12 hours in order to kill *Yersinia sp.*, a psychrophilic bacterium that is a major contaminant of blood. As shown, it is expected that such blood will have low levels of DPG and hence be suboptimally functional on transfusion.

An experiment was devised to determine whether the DPG levels could be brought back to approximate initial levels, that is, whether the RBC could be rejuvenated. Whole blood with heparin as anticoagulant was held at room temperature for 6 days, at which time DPG levels were undetectable. D-ribose at 10 mM was added and the blood was incubated at 37° C. for thirty minutes. At the end of the incubation, DPG was assayed again and was found to have increased to about one-third of the usual initial value. The incubation time will be extended to determine whether the DPG levels can be further increased.

Figure 2:
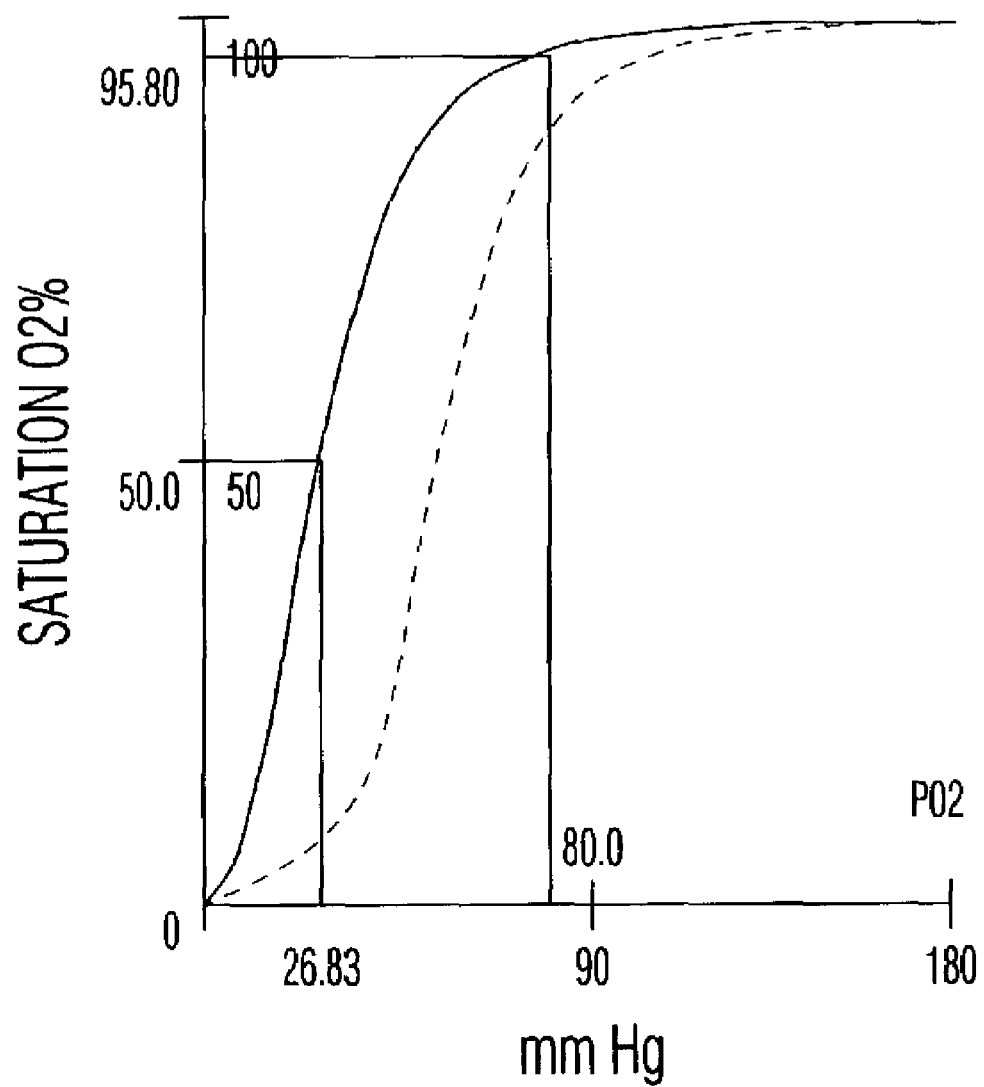
FIG. 2 shows the effect of 2,3 diphosphoglycerate levels on the oxygen-hemoglobin dissociation curve.

B. A direct measure of RBC function is the oxygen dissociation curve. When the percent saturation of oxygen in blood is plotted against the partial pressure of oxygen (mmHg), the resulting curve is shown in FIG. 2. A shift to the right occurs when DPG is increased or pH is decreased. Consistent with the DPG experiments, the oxygen tension giving 50% saturation (P50) after six days storage in CPD was 43 mmHg. When this sample was rejuvenated as for Example 3A above, the P50 was 18.2 mmHg.

EXAMPLE 5

Glycolytic Intermediates Enhancing the D-Ribose Effect.

Figure 3:
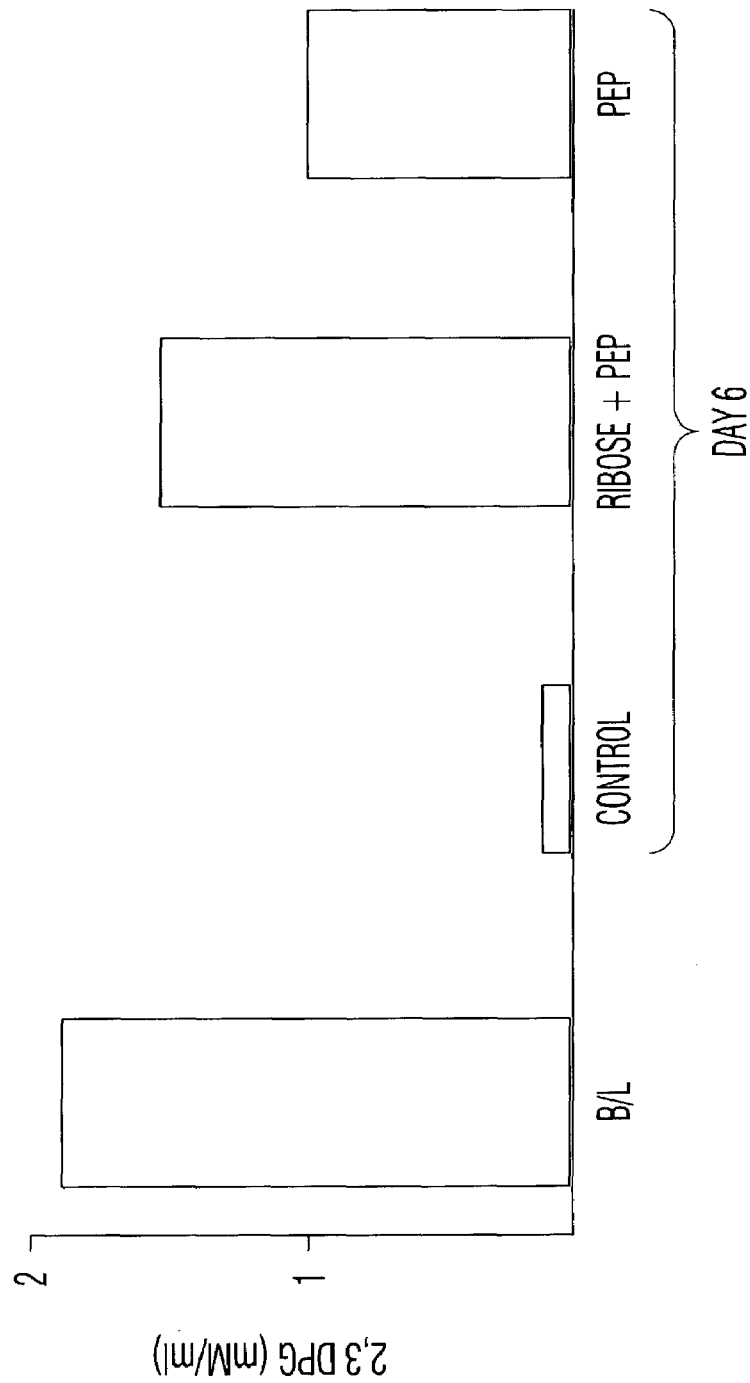
FIG. 3 shows the rejuvenation of blood cells by ribose and phosphoenolpyruvate as measured by an increase in 2,3 diphosphoglycerate.

The rejuvenation experiment of Example 4 was repeated adding the high energy glycolysis intermediate phosphoenolpyruvate (PEP). Samples were held at for six days at room temperature until DPG levels were barely detectable. At that point, 15 mM D-ribose, 10 mM to 100 mM PEP or both were added and the blood incubated at 37° for 30 minutes. As seen in FIG. 3, the DPG levels decreased from about 2 µmol/ml to barely detectable levels at day 6. Adding PEP gave some benefit, raising the DPG levels to nearly 1 µmol/ml. Ribose also raised levels to about 1 µmol/ml. The effect of ribose plus PEP was additive: levels exceeded 1.5 µmol/ml, nearly the levels on day 0.

These results may indicate that the rejuvenating RBCs have stepped up glycolytic pathways. Although ribose can act as an energy source, it is possible that its conversion to glucose-6-phosphate for entry into the glycolytic pathway is slow. Therefore, adding a glycolytic intermediate such as PEP was shown to enhance the ribose effect, possibly by providing additional energy. Other glycolytic substrates and intermediates such as glucose, glucose-6-phosphate, fructose-6-phosphate, and pyruvate are likewise expected to enhance the ribose effect on rejuvenating RBCs.

This invention has been described in terms of certain embodiments. Following the teachings of this application, those skilled in the art can easily make substitutions and modifications to the embodiments without departing from the spirit and scope of the invention. Therefore, such substitutions and modifications are within the scope of the appended claims. All references cited within are hereby incorporated by reference.

We claim:

1. A method for rejuvenating red blood cells, the method comprising:
    providing red blood cells that have been stored in the absence of a ribose-related compound for at least 42 days to result in a decrease in the 2,3-diphosphoglycerate (DPG) level from the freshly drawn value;
    adding sufficient ribose-related compound to a suspension of said red blood cells so as to reach a concentration of 5 to 20 mM, wherein the ribose-related compound is selected from the group consisting of D-ribose, ribose-5-phosphate, ribulose-5-phosphate, ribulose, xylulose-5-phosphate, xylulose, xylose, and xylitol; and
    incubating the cells at 37° C. for 10 to 60 minutes wherein the DPG levels are increased to at least one-third of the freshly drawn value.

2. The method of claim 1 wherein the ribose-related compound is 10mM D-ribose and the cells are incubated at 37° for 30 minutes.

3. The method of claim 1 wherein the red blood cells are suspended in whole blood or are packed red blood cells.

4. The method of claim 1 further comprising, prior to incubating, adding sufficient phosphoenolpyruvate to the suspension of said red blood cells that have been stored for at least 42 days so as to reach a concentration of 10 mM to 100 mM.

5. The method of claim 1 wherein the red blood cells have been stored at 4° C. for at least 42 days.

6. The method of claim 1 wherein the freshly drawn DPG value is about 2 µmol/ml.

7. A method for rejuvenating red blood cells, the method comprising:
    providing red blood cells that have been stored in the absence of a ribose-related compound for at least 21 days to result in a decrease in the 2,3-diphosphoglycerate (DPG) level from the freshly drawn value;
    adding sufficient ribose-related compound to a suspension of said red blood cells so as to reach a concentration of 5 to 20 mM, wherein the ribose-related compound is selected from the group consisting of D-ribose, ribose-5-phosphate, ribulose-5-phosphate, ribulose, xylulose-5-phosphate, xylulose, xylose, and xylitol; and
    incubating the cells at 37° C. for 10 to 60 minutes wherein the DPG levels are increased to at least one-third of the freshly drawn value.

8. The method of claim 7 wherein the red blood cells have been stored at 4° C. for at least 21 days.

9. The method of claim 7 wherein the freshly drawn DPG value is about 2 µmol/ml.

* * * * *